(12) United States Patent
Dalton et al.

(10) Patent No.: US 10,251,994 B2
(45) Date of Patent: Apr. 9, 2019

(54) TRANSPLANTED CELL CONTAINMENT AND NUTRITION DEVICE

(71) Applicants: Michael J. Dalton, Evanston, IL (US); Jordan M. Dalton, Libertyville, IL (US); Natan A. Pheil, Chicago, IL (US)

(72) Inventors: Michael J. Dalton, Evanston, IL (US); Jordan M. Dalton, Libertyville, IL (US); Natan A. Pheil, Chicago, IL (US)

( * ) Notice: Subject to any disclaimer, the term of this patent is extended or adjusted under 35 U.S.C. 154(b) by 56 days.

(21) Appl. No.: 14/182,418

(22) Filed: Feb. 18, 2014

(65) Prior Publication Data
US 2014/0236078 A1    Aug. 21, 2014

Related U.S. Application Data

(60) Provisional application No. 61/766,111, filed on Feb. 18, 2013.

(51) Int. Cl.
| *A61M 5/142* | (2006.01) |
| *A61M 5/14* | (2006.01) |
| *A61M 5/172* | (2006.01) |
| *A61F 2/02* | (2006.01) |

(52) U.S. Cl.
CPC .......... *A61M 5/1407* (2013.01); *A61F 2/022* (2013.01); *A61M 5/14276* (2013.01); *A61M 5/1723* (2013.01); *A61M 2005/14208* (2013.01); *A61M 2202/09* (2013.01)

(58) Field of Classification Search
CPC . A61F 2/022; A61M 5/1723; A61M 5/14276; A61M 5/1407; A61M 2202/09; A61M 2005/14208; A61M 5/14244; A61M 2230/201

USPC ....................... 604/66, 890.1–892.1, 151, 59
See application file for complete search history.

(56) References Cited

U.S. PATENT DOCUMENTS

| 3,738,365 | A |   | 6/1973 | Schulte |   |
| 3,750,194 | A | * | 8/1973 | Summers | A61F 2/004 |
|  |  |  |  |  | 128/DIG. 25 |
| 4,368,737 | A | * | 1/1983 | Ash | A61M 1/285 |
|  |  |  |  |  | 604/175 |
| 5,011,472 | A | * | 4/1991 | Aebischer | A61F 2/022 |
|  |  |  |  |  | 604/153 |
| 5,425,764 | A | * | 6/1995 | Fournier | A61F 2/022 |
|  |  |  |  |  | 604/6.09 |
| 6,217,609 | B1 |   | 4/2001 | Haverkost |   |
| 6,511,473 | B2 | * | 1/2003 | Bartha | C12N 5/0677 |
|  |  |  |  |  | 604/890.1 |
| 7,043,295 | B2 | * | 5/2006 | Starkebaum | A61F 5/0026 |
|  |  |  |  |  | 600/546 |

(Continued)

OTHER PUBLICATIONS

STIC Search, Sep. 1, 2015.*

(Continued)

*Primary Examiner* — Bhisma Mehta
*Assistant Examiner* — Hamza A Darb
(74) *Attorney, Agent, or Firm* — Klintworth & Rozenblat IP LLP

(57) ABSTRACT

The disclosure provides an implanted device that promotes the protection and maintenance of transplanted cells in a host body. The implanted device provides the transplanted cells with a safe, nutritious environment for survival and removes waste products generated by the cells.

45 Claims, 15 Drawing Sheets

(56) References Cited

U.S. PATENT DOCUMENTS

| | | | |
|---|---|---|---|
| 2004/0024358 A1 | 2/2004 | Meythaler | |
| 2006/0089619 A1* | 4/2006 | Ginggen | A61M 5/14276 604/891.1 |
| 2006/0127246 A1* | 6/2006 | Forsell | A61M 5/1428 417/412 |
| 2008/0039792 A1 | 2/2008 | Meng | |
| 2009/0287178 A1 | 11/2009 | Herbert | |
| 2009/0318844 A1 | 12/2009 | Burnett | |
| 2010/0204683 A1* | 8/2010 | Bodor | A61F 2/022 604/891.1 |
| 2010/0228179 A1 | 9/2010 | Thomas | |
| 2012/0172782 A1 | 7/2012 | Thompson | |
| 2013/0289540 A1* | 10/2013 | Zeltser | A61M 5/14276 604/891.1 |
| 2014/0155806 A1 | 6/2014 | Cheng | |

OTHER PUBLICATIONS

Non-Final Office Action for U.S. Appl. No. 14/662,986, dated Sep. 28, 2017, 9 pages.
Non-Final Office Action for U.S. Appl. No. 14/796,927, dated Apr. 19, 2018, 12 pages.

* cited by examiner

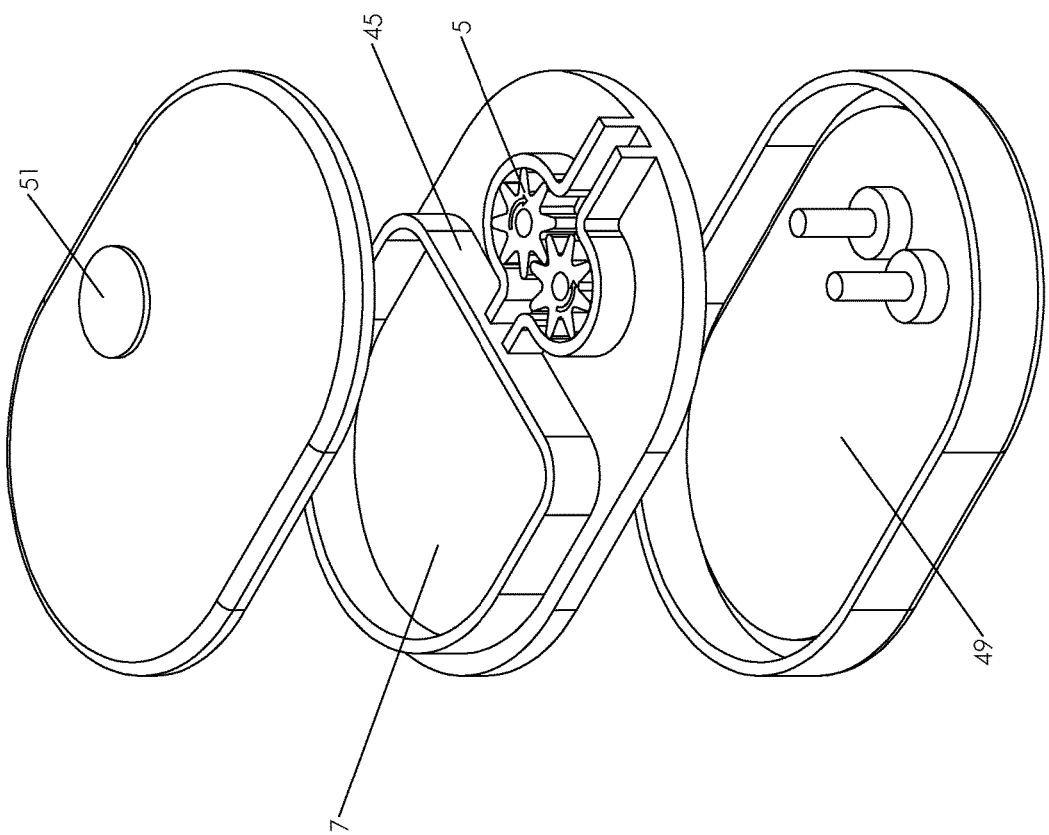

TRANSPLANTED CELL CONTAINMENT AND NUTRITION DEVICE

The present application claims priority to the U.S. Provisional Application 61/766,111, filed on Feb. 18, 2013, by the same applicant.

BACKGROUND

Diabetes mellitus is a chronic debilitating disease affecting over 170 million people worldwide, 5-10% of which, about 8.5 to 17 million, are type 1 diabetic (T1D) patients. T1D patients inject insulin daily to control blood glucose (BG), however, BG fluctuations and impaired glycemic control inherent to exogenous insulin administration is associated with severe complications in the long term. Consequently, diabetes is one of the leading causes of blindness, end-stage renal failure, non-traumatic limb amputations, and cardiovascular morbidity and mortality. Quality of life for diabetic patients is evidently decreased, not only in manifestation of complications, but also in managing the disease and fear of life threatening glycemic events. Cell-based therapies such as, replacement of the insulin producing pancreatic-cells by transplanting isolated human islet cells intraportally is an approach that has shown remarkable promise in restoring normoglycemia. In turn islet allotransplants have reduced the incidence for frequent and life-threatening complications associated with metabolic instability. However, a shortage of human donor pancreases exists, limiting the number of patients that can take advantage of this therapy. Exacerbating this are intraportal islet transplant protocols that require high islet numbers as a consequence of the significant loss of islets (over half is speculated) immediately post transplant to hypoxia, inflammation, and immune-mediated loss. There is general agreement that the liver may not be the ideal environment for islets because of exposure to high concentrations of glucagon, diabetogenic immunosuppressive drugs, and toxins from the gastrointestinal tract. For these reasons, and causes not fully understood, intrahepatic islets in humans exhibit a progressive loss of function. This suggests that an alternative implantation site is critically needed to achieve long-term diabetes reversal and preserve the short supply of available cells for transplantation. In the future it is likely that additional sources of cells will be an option for patients as promising results with porcine islets have been achieved in nonhuman primates. Furthermore, several groups have derived islet progenitors or differentiated cells from pluripotent stem cells. It is reasonable to expect that these cells would encounter similar challenges that have been observed in human allogeneic islet transplants if delivered intraportally. Devices that enable alternative islet transplantation sites by addressing the basic yet vital needs of islets (e.g. oxygen, nutrition, hydration, and waste disposal) have potential to enhance the translational value of these promising therapies. A number of alternative sites have been evaluated along with immune-isolation or encapsulations technologies. These approaches have a range of limitations that include premature death of the cells, inability to measure the health of the transplanted cells and the inability to retrieve the encapsulated dead cells.

There is significant interest in the field of transplanted cells, more specifically for the Islets of Langerhans preservation and immunoisolation devices. The potential for an immunoisolation device ranges from the use of transplanted porcine islet cells, to the preservation of Induced Pluripotent Cells, both for the diabetic patient population to introduce or create a plentiful supply of functioning islet cells. In addition to the use of such a device in transplanted islets, numerous other applications for transplanted cells exist.

Therefore, there exists a need for a dynamic bio-artificial pancreas, a cell transplant device designed to be a cell oasis to protect and nourish transplanted cells. The present invention will alleviate the major problems associated with islet cell loss in the engraftment phase to long-term and promote the development of an alternative islet transplantation site.

BACKGROUND OF THE INVENTION

All living cells in the body require three things to survive 1) oxygen, 2) nutrition, and 3) hydration. Ideally, in addition to nutrition, the waste products from the transplanted cells should be removed as needed. In the living body, both human and animal, these functions or requirements are supplied by the interstitial fluid that surrounds all cells. In the case of transplanted cells, these cells additionally need to be protected from the immune system of the host. Therefore, these cells need a protected filtered environment that prevents the components of the immune system from destroying them.

The present invention is directed to an apparatus or device that provides both immuno-protection and nutrition to transplanted cells. The invention is comprised of three (3) separate chambers and mechanisms that when combined provide a system for immuno-protection and for providing fluids required to sustain life.

Diabetes is a group of diseases characterized by high levels of blood glucose resulting from defects in insulin production, insulin action or both. The major types of diabetes include type 1 diabetes, type 2 diabetes, gestational diabetes, and pre-diabetes. Type 1 diabetes, also referred to as insulin-dependent diabetes mellitus (IDDM) or juvenile-onset diabetes, results when the body's immune system destroys insulin producing pancreatic beta cells. Type 1 diabetes accounts for approximately 5-10% of all diagnosed cases. Type 2 diabetes, also referred to as non-insulin dependent diabetes mellitus (NIDDM) or adult-onset diabetes, results from insulin resistance, combined with relative insulin deficiency. Type 2 diabetes represents approximately 90% of all diagnosed cases.

Diabetes mellitus is a chronic debilitating disease affecting over 170 million people worldwide, 5-10% of which, about 8.5 to 17 million, are type 1 diabetic patients. Diabetes is one of the leading causes of blindness, end-stage renal failure, non-traumatic limb amputations, and cardiovascular morbidity and mortality. Quality of life for diabetic patients is evidently decreased, not only in manifestation of complications, but also in managing the disease and fear of life threatening glycemic events.

Patients with type 1 diabetes must have insulin delivered via injection or pump in order to survive. In its early stages, some people with type 2 diabetes can manage the disease through a combination of drugs that increase pancreatic insulin, or act on the liver, muscle or intestine, plus lifestyle changes in diet and exercise. However, despite these efforts, 40% of all type 2 diabetic patients eventually require injections of insulin.

The most promising treatment for both type 1 and type 2 diabetes may be the replacement of damaged pancreatic beta cells with intact functioning beta cells through beta islet transplantation. Cell-based therapies, replacement of the insulin producing pancreatic-cells by transplanting isolated human islet cells intraportally is an approach that has shown remarkable promise in restoring normoglycemia. In turn islet allotransplants have reduced the incidence for frequent and life-threatening complications associated with metabolic instability. However, a shortage of human donor pancreases exists, limiting the number of patients that can take advantage of this therapy. Exacerbating this are intraportal islet transplant protocols that require high islet numbers as a consequence of the significant loss of islets (over half is speculated) immediately post transplant to hypoxia, inflammation, and immune-mediated loss. There is general agreement that the liver may not be the ideal environment for islets because of exposure to high concentrations of glucagon, diabetogenic immunosuppressive drugs, and toxins from the gastrointestinal tract.

However, there remain major limitations associated with the therapy—i.e. the loss of beta cell viability and function due to the lack of a blood supply and oxygen and nutrients to support cell viability. The present invention is directed to address such limitations.

The present invention is comprised of: an interstitial fluid accumulation chamber/area; a pumping mechanism that will transfer the fluid from the interstitial accumulation chamber/area to the cell containment chamber, and a cell containment chamber/isolation chamber designed to contain the transplanted cells and protect them from the host's immune system. These three mechanisms may be individual components that may be implanted separately in various areas of the body or may be combined in one single structure. Thus, the invention may be constructed such that the mechanisms may be constructed in a single structure or as three separate components wherein each component is connected via a pathway or connector.

The present invention uses the combination of three mechanisms in a novel and unique manner. The present invent comprises a singular, compact device combining three separate mechanisms in a manner that would provide isolation, nutrition, and oxygen to the transplanted cells. While it is important to isolate and protect the transplanted cells, one of the innovative features of this invention is the use of an interstitial fluid accumulation chamber that is placed in the subcutaneous space to collect interstitial fluid and a pumping mechanism to deliver the collected interstitial fluid to the cells contained in the isolation chamber. The combination of the three mechanisms in one system would provide the transplanted cells with a safe, nutritious environment for survival and would also be suitable for removal of the waste products generated by the cells. An innovative feature of this design is to use the host's interstitial fluid, suitably filtered to remove any potentially fatal immune system cells, to sustain the transplanted cells.

The interstitial fluid that occurs in the subcutaneous space is believed to have abundant oxygen and nutrition to allow the transplanted cells to survive and flourish. Such findings have been found in the testing of Lewis rats. A unique aspect of this design is that the cells will be supplied with adequate oxygen and nutrition from the interstitial fluid while in the isolation chamber. The interstitial fluid will be collected and pumped to the transplanted cells. The degree and timing of the pumping of the fluid into the isolation chamber will be dependent on three issues 1) the concentration of oxygen and nutrition in the interstitial fluid; 2) the needs of the cells; and 3) the production of insulin required by the host. The amount and frequency of the pumping and fluid delivery may be fully controllable.

Another innovative aspect of this invention is to include a "port" connected to the isolation chamber such that the transplanted cells can be delivered to the isolation chamber after the device has been allowed to stabilize within the host's body. Additionally, with this port or access point, the quality of the cells and the fluid within the chamber can be easily monitored as well. The "port" or implanted vascular access device is a well-known product used in animal research and in human oncology for long-term vascular access. A port or vascular access device is comprised of a puncture-capable silicone rubber septum placed over or covers an accumulation chamber or reservoir with an outlet. This design allows for a needle of appropriate size to be inserted into the chamber through the septum to deliver the contents of an attached syringe or to remove fluid from the chamber. When the needle is removed, the puncture point of the septum closes to provide a sealed environment within the chamber. The use of a "port" is a unique feature of the present invention. It allows the researcher or physician to monitor, adjust, remove, and/or reintroduce the cells or to simply add drugs to further enhance or adjust the health of the cells contained in the isolation chamber.

The design of the present design is such that the insulin produced by the cells in the isolation chamber can be delivered into the subcutaneous environment or to a remote site if that is deemed the best therapeutic approach. Insulin could be delivered to the peritoneal cavity or the portal vein or any other suitable area or vessel through the use of a special silicone catheter placed at the outlet of the Isolation or cell containment chamber of the present invention.

The overall design of the present invention is to provide the transplanted/isolated cells with adequate amounts of oxygen and nutrient containing fluid to maintain cell integrity. The present invention further removes the cellular waste along with the insulin that is washed from the isolation chamber on an as needed basis.

All components may be fabricated of biocompatible and pliable elastomeric material preferably Medical grade silicone rubber or elastomeric material and medical grade metals such as Titanium or stainless steel.

SUMMARY OF THE INVENTION

The present invention is directed to a device to be implanted to act as a bio-artificial pancreas or host site containing transplanted cells. More particularly, the present invention is directed to a device that promotes the protection and nourishment of transplanted cells in a host.

For a variety of applications, ranging from medical research to therapeutic use, it is desirable to implant such a device in the subcutaneous tissue of the host where the body protects the device and the interstitial fluid used in the maintenance of the transplanted cells is abundant.

DESCRIPTION OF THE DRAWINGS

FIG. 15 is an exploded isometric view of an embodiment of the present invention.

DESCRIPTION OF THE INVENTION

Figure 1:
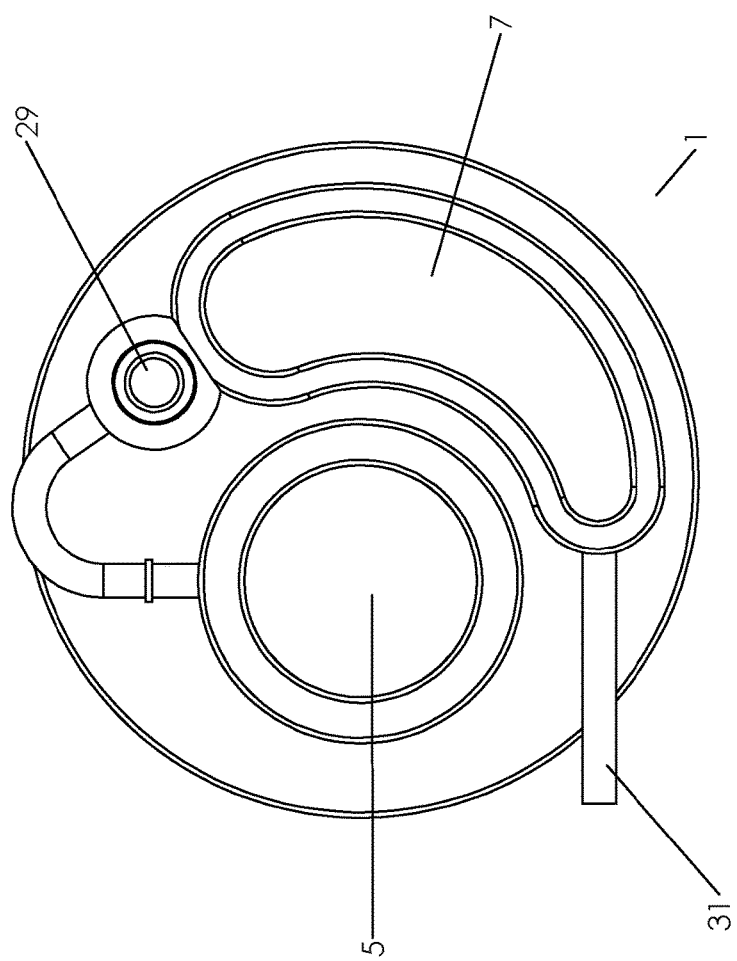
FIG. 1 is a top view of an embodiment of the present invention.
Figure 2:
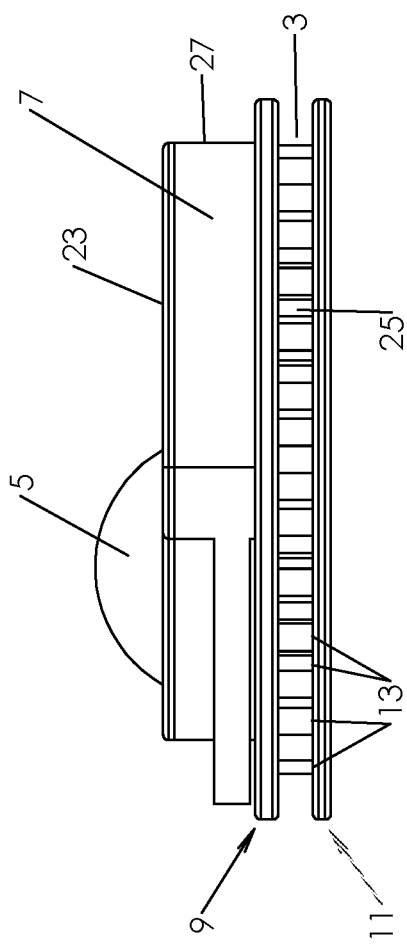
FIG. 2 is a side view of an embodiment of the present invention.
Figure 3:
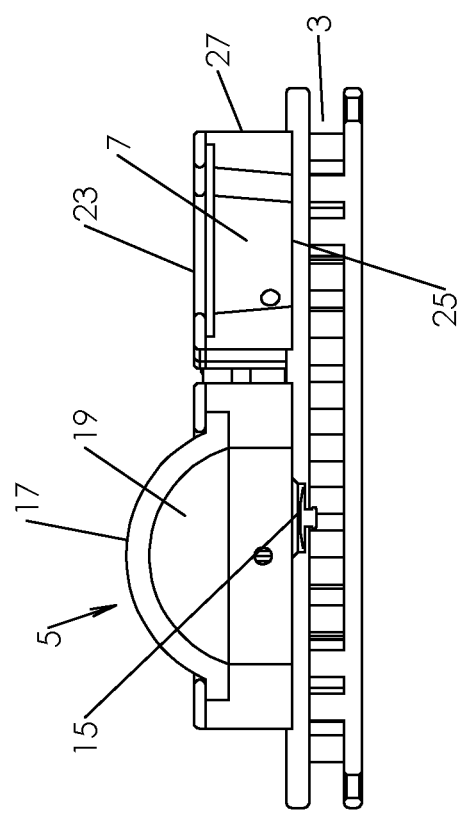
FIG. 3 is a cross sectional view of an embodiment of the present invention.
Figure 4:
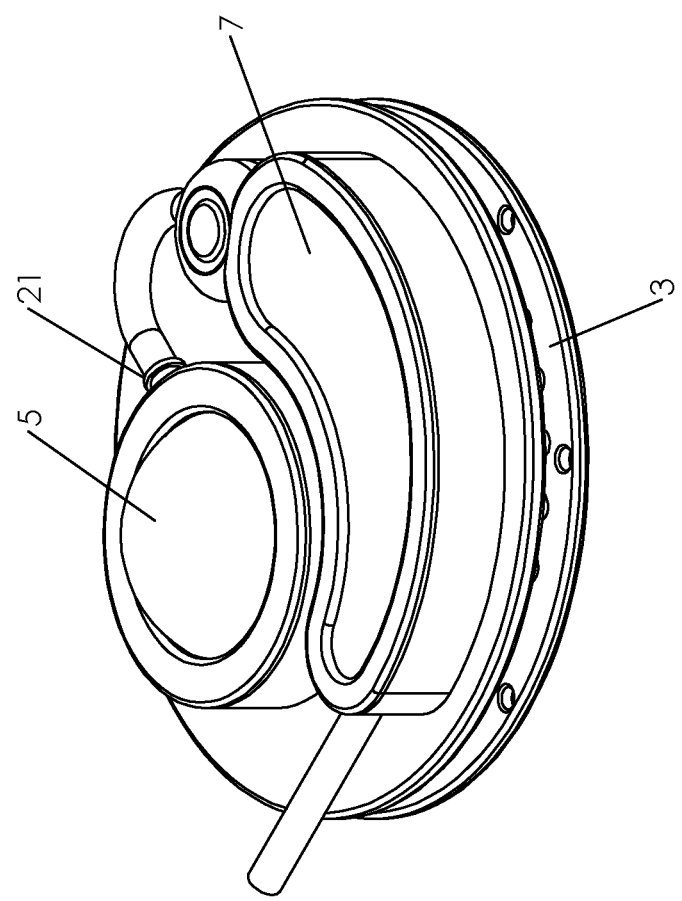
FIG. 4 is a perspective view of an embodiment of the present invention.

This present invention provides an implanted device that promotes the protection and maintenance of transplanted cells in a host body.

In one embodiment of the present invention, as illustrated in FIGS. 1, 2, 3 and 4, the invention shown generally as 1 is comprised of an interstitial fluid accumulation chamber/area 3, a pumping mechanism 5 that will transfer the fluid from the interstitial accumulation chamber/area to the cell containment chamber/isolation chamber 7, and a cell containment chamber/isolation chamber 7 designed to contain the transplanted cells and protect them from the host's immune system.

Interstitial Fluid Accumulation Area

Cells in a living body obtain their nutrition and oxygen from the interstitial fluid around them. The nutrition and oxygen in the interstitial fluid is transferred there by the host's blood stream and delivered to the cells in the interstitial fluid. The interstitial fluid contains enough oxygen and nutrition to keep the cells alive and flourishing as though they were in a compatible environment. To supply transplanted cells with the necessary nutrients and oxygen supply, the present invention provides an isolated protected chamber, mechanism or area that allows all of the required fluid to be accumulated. Interstitial fluid needs to be accumulated in a specific area and transferred to the cell containment chamber 7 on an as needed basis. The present invention addresses such need by creating a cavity or space in the subcutaneous tissue via the interstitial fluid accumulation chamber, mechanism or area 3. The accumulated interstitial fluid is then pumped to a cell containment area 7 via a pumping mechanism 5.

The fluid accumulation within the interstitial fluid accumulation chamber, mechanism, area 3 will occur rapidly and continuously over time and be sufficient to supply all of the nutritional needs of the transplanted cells.

In one embodiment of the present invention, the interstitial fluid accumulation chamber 3 is a chamber having a top plate 9 and a bottom plate 11 held apart by a plurality of posts 13 that extend from the top surface of the bottom plate 11 to the bottom surface of the top plate 9. The area between the top plate 9 and the bottom plate 11 is determined by the volume of the fluid that needs to be accumulated. The plurality of posts 13 are placed around the periphery or outer edge of the accumulation chamber, mechanism area 3 to create a tortuous path for tissue to grow into and prevent the tissue ingrowth from totally penetrating the center space of the chamber 3. The distance between the plates is predetermined to prevent tissue from growing over the plates and occluding them.

The top and bottom plates 9 and 11 may be fabricated of pliable silicone rubber. The top and bottom plates 9 and 11 are held apart by a plurality of posts 13 or columns in the interior of the disk. The inlet/outlet catheter 15 is in the center of the disk and is protected from the host's invading tissue by the posts that create a torturous path for tissue invasion and preventing the center from being engulfed. The top and bottom plates 9 and 11 are spaced apart such that the tissue that would engulf a catheter or a small device will not grow across the gap created between the top and bottom plates 9 and 11. While the top and bottom plates 9 and 11 of the disk may become engulfed with tissue, the center of the device will remain open and allow for fluid accumulation.

In another embodiment, the posts 13 or columns between the top 9 and bottom plates 11 may be replaced with a suitable filter material or a metallic screen or mesh or plurality of such materials. The purpose of these elements is simply to prevent tissue from growing into the center space.

In another embodiment, filters or tissue preventing mesh or means may be used in the accumulation chamber/area 3 in order to prevent tissue from growing into the center space of the accumulation chamber/area 3. In one embodiment, filters may replace the outlet/catheter 15 in the isolation chamber 7 to allow fluid to be dispersed into the interstitial space and to keep the isolated cells from escaping the isolation chamber 7.

Also it is important for the fluid that is accumulated to be free from debris and the defense mechanisms of the host. In one embodiment, a filter may be included around the center of the interstitial fluid accumulation chamber 3 to protect the cells from the hosts' immune system's killer cells.

Once adequate interstitial fluid has been accumulated in the accumulated interstitial fluid chamber 3, such interstitial fluid must be flowed to the pumping mechanism 5. To accomplish this, a catheter or outlet 15 is positioned at the bottom center of the bottom plate 11 or in the center of the top plate 9 of the accumulated interstitial fluid chamber 3 providing a pathway to the pumping mechanism 5. The bottom plate 11 of the accumulated interstitial fluid chamber 3 is semi-rigid to contour to the host's body structure. The top plate 9 may have an outside ring or diameter of semi-rigid material while the center is thinner elastic silicone rubber.

In one embodiment, the volume of the accumulated interstitial fluid chamber 3 is approximately 4 cc's with the elastic center volume being approximately 3 cc's. As the pumping mechanism 5 is activated, fluid is forced from the pump area 5 into the cell containment chamber 7. When the pump 5 is released, the restoring force of the pumping mechanism will create a negative pressure within the pumping area and due to this negative pressure the elastic top 17 of the accumulated interstitial fluid chamber 3 will be drawn down. With such negative pressure, fluid is withdrawn from the accumulated interstitial fluid chamber 3 into the pump area 5. Due to the elastic nature of the elastomeric material and the restoring force of the pumping mechanism, negative pressure will be maintained until the pump mechanism is filled with interstitial fluid and the system returns to the resting state.

To prevent interstitial fluid from flowing back towards the accumulated interstitial fluid chamber 3, an inlet check valve or simple backflow mechanism is present in the pathway between the accumulated interstitial fluid chamber and the pump area. The negative pressure in the pump area once the pump is released will cause the inlet check valve to stay open and keep the outlet side check valve closed.

Pump:

In the present invention, the pump 5 may be comprised of a chamber having an elastomeric dome 17 that may be depressed or activated to cause interstitial fluid to be withdrawn from the pumping chamber 19 to the cell containment chamber 7.

In one embodiment, the pump 5 will require manual operation. The user will physically press the dome 17 of the pump to move the fluid from inside of the pumping chamber 19 to the cell isolation chamber 7. In one embodiment, the dome 17 may be constructed of a simple silicone rubber dome fabricated of 60 durometer silicone having a wall thickness of 0.010" to 0.100" and has a semi-ridged or ridged bottom. The volume of the pumping chamber 19 may be approximately 3 cc's in fluid volume. The pumping mechanism 5 additionally has at least one inlet and at least one outlet 21. The at least one inlet and outlet have one-way valves or check valves to allow flow out of the accumulated interstitial fluid chamber to the pumping chamber 19 and from the pumping chamber 19 to the cell isolation chamber 7. Interstitial fluid flows from the pumping chamber 19 to the cell containment chamber 7 once the dome 17 is depressed or activated and interstitial fluid flows into the dome 17 from the accumulated interstitial fluid chamber 3 once the volume is discharged from the pumping chamber 19. When the positive external pressure is released and the pumping chamber 19 is allowed to refill and return to the resting state, the retaining force of the silicone dome 17 will create a small negative pressure that will draw interstitial fluid into the pumping chamber 19 from the accumulated interstitial fluid chamber 3.

In one embodiment, the pumping mechanism is comprised of a pumping chamber 19, a simple silicone dome 17, and check valves or duck bill valves at both the inlet and outlet of the pumping chamber. Pressing the top of the dome 17 will force the accumulated interstitial fluid from the pumping chamber 19 into the cell containment chamber 7. When the pressure or dome 17 is released, the elastic properties of the flexible dome 17 will draw fluid into the pumping chamber 19 from the accumulated interstitial fluid chamber 3, that is, after the dome 17 is pressed and the fluid is expelled, the elastic restoring force of the dome 17 will create a negative pressure in the pumping chamber 19 and draw fluid from the accumulated interstitial fluid chamber 3 into the pumping chamber 19 over time. The check valves will allow flow in only one direction, i.e., from the accumulated interstitial fluid chamber 3 to the pumping chamber 19 and from the pumping chamber 19 to the cell containment chamber 7.

In another embodiment, the pumping mechanism 5 may employ an electric motor, i.e., a linear peristaltic, a rotary peristaltic or a simple piston metering programmable pump that would more accurately and precisely deliver the accumulated fluid to nurture the transplanted cells. Additionally, the pump 5 could communicate with a glucose sensor in the fluid accumulation chamber to provide feedback and, thus, better control of the insulin needs of the patient. Additionally, the pumping mechanism 5 may be controlled via a computer, micro-processor, sensor or monitor to be engaged or controlled independently of user manual manipulation.

In the case of the type 1 diabetic, until the communication between the vascular system and the cells is established and the delivery of the insulin is automatic, the distinct advantage of the pumping mechanism 5 is that as the insulin is needed, as determined by a glucose sensor, the pump 5 can be actuated to supply the required insulin by the host. Or the pump can be pressed routinely before meals to provide a needed bolus of insulin. After the communication is established, the pump 5 would be activated on some routine basis simply to supply the transplanted cells with oxygen and nutrition and remove cellular waste.

Transplanted Cell Isolation Chamber/Cell Chamber:

The function of the cell containment chamber 7 is to protect and allow the cells contained within it to flourish and be protected from the hostile environment of the host. Much has been written and directed to providing an environment inside a host body where the cells are protected from the body's immune system. The cell containment chamber 7 may be comprised of a biocompatible enclosure or chamber. The cell containment chamber 7 may be constructed specifically of silicone rubber with a top portion 23, bottom portion 25 and periphery walls 27. A portion of the bottom of the chamber 25 may be comprised of a semipermeable filter membrane. This membrane is porous to the fluids produced by the cells yet a barrier to the host's immune system—particularly the host body's NK cells, "T" cells and B cells. Typically the immune system's cells are in the range of 4-12 microns. In one embodiment of the present invention, the bottom of the chamber 25 is constructed of a filter material with pore size 1 micron although other size filters and other placements of the filter are possible. The surface of the bottom portion of the chamber 25 may be enhanced with a hydrogel compound on which the transplanted cells will thrive. In one embodiment, a cellular matrix or scaffold material may be present in the interior of the cell containment chamber 7. The use of such matrix and scaffold material is well known in other devices. The size of the chamber may be typically approximately between 1.0 and 5.0 cc's in volume. This volume is selected for the ability to contain approximately 100,000 to as much s 400,000 islets. An amount determined to product enough insulin to maintain glycemic status quo.

In one embodiment, the cell containment chamber 7 may be cylindrical in shape and may be possibly be 1" in diameter. The top portion 23 may be elastomeric in material to expand to contain approximately 3 cc's of fluid pumped into the cell containment chamber 7 by the pumping mechanism 5. The bottom portion 25 of the cell containment chamber 7 will be comprised of a composite material of an appropriate filter material and a Dacron felt or velour material to promote vascularization close to the cells within the chamber 7. The interstitial fluid that is pumped into the cell containment chamber 7 will diffuse out of the bottom portion of the cell containment chamber 7 through a filter material. When the pumping mechanism 5 is activated, the flexible elastomeric top 23 of the cell containment chamber 7 is expanded due to the increased fluid entering the cell containment chamber 7 and the fluid will be "pushed" out through the porous bottom portion 25 of the cell containment chamber 7 slowly and into the host's interstitial fluid and blood stream. The size and porosity of the bottom portion 25 and filter material will be adjusted to restrict the outflow such that the inflow of interstitial fluid will mix with the cell producing enzymes and flow out as a combined fluid. It is important to not only provide the living cells with nutrients, but also to remove the waste products of the living cells. The flow of fluid through the cell containment chamber 7 will accomplish this.

In one embodiment, the volume of the chamber 7 will be approximately 5 cc's to accommodate ~500,000 Islet of Langerhans cells. The top of the cylinder 23 will be covered with flexible, elastic silicone that will expand when the interstitial fluid is pumped into the chamber 7. The memory of the elastic silicone will provide a restoring force on the fluid to push it through the bottom filter, thereby flushing the cells with oxygenated nutritious fluid and carrying the waste products away. The flow and dwell time for the interstitial fluid will be determined by both the pore size and the overall size of the filter window.

In order to monitor the cell containment chamber 7, a small compressed silicone septum window/portal 29 may be placed adjacent to the cell containment chamber 7 to sample fluid and to withdraw and replenish the cells in the cell house if necessary. Alternatively, the septum window/portal 29 may be incorporated in the top surface of the cell containment chamber 7. Additionally angiogenesis drugs can be injected/infused through the portal 29 to promote vascularization outside of the cell house base. Vascularization is important for communications between the cells and the blood stream. Ideally this communication will be both ways, from the cells out and from the vasculature into the cell chamber to elicit the production of the enzymes designated by the transplanted cells.

As illustrated in FIGS. 1, 2, 3, and 4, the interstitial fluid accumulation chamber 3, the pumping mechanism 5 and the cell containment chamber 7 may be constructed in a single housing wherein each component may be adjacent to one another in a linear fashion. In another embodiment, each component may be connected to one another in a singular housing wherein the components form a triangular overall structure. In another embodiment, the components may be connected to one another in a circular fashion such that each component is concentric to one another.

As illustrated in FIGS. 7, 8, 9 and 10, each component may be connected via a pathway in a linear fashion. In one such embodiment, each component may be placed in a different area within the host body.

The overall size of the present invention may be controlled by two elements: 1) the isolation or cell containment chamber size, and 2) the pump capacity. It is estimated that an islet of Langerhans cell count of 500,000 would be required for normal glycemic control in an adult. This amounts to a volume in the isolation chamber of approximately 5 cc's. And 2) the pumping mechanism is designed at an equivalent 5 cc's.

In one embodiment, the device may be round in shape. In such embodiment, the specifications are that the diameter will be less than 2.5"/64 mm in diameter and 0.625"/16 mm in height or thickness. At this diameter and thickness, placement anywhere in the human body is a possibility. For research applications, where a smaller isolation chamber is required that is, less than 5 cc's, a smaller size and different configuration is highly possible.

As illustrated in FIGS. 1, 2, 3, 4, 5 and 6, in one embodiment of the present invention, the interstitial fluid accumulation chamber 3 may be in an area beneath the pumping chamber 5 and is comprised of a top plate 9 and a bottom plate 11 held apart by a plurality of posts 13 that extend from the top surface of the bottom plate 11 to the bottom surface of the top plate 9. In this embodiment, the top plate 9 has an opening 15 leading to the bottom portion of the pumping chamber 19 which has a corresponding opening. Once adequate interstitial fluid has been accumulated in the accumulated interstitial fluid chamber 3, fluid will flow from the interstitial fluid accumulation chamber to the pumping chamber. In order to prevent fluid flowing back to the interstitial fluid accumulation chamber 3, an umbrella style check valve or back flow valve is present in the opening between the top plate 9 of the interstitial fluid accumulation chamber 3 and the bottom portion of the pumping chamber 19.

In one embodiment, when the pumping mechanism 5 is activated or the dome 17 of the pump is depressed the fluid present in the pump 17 will be forced through a port 29 that is connected to the cell containment chamber 7 and then to the cell containment chamber 7. The port 29 may be a standard access port with a reservoir and silicone septum that allows a user to access the reservoir. The cell containment chamber 7 may be a chamber that is connected to an outlet catheter or tube 31. As the pump 5 is depressed, pressure forces the valve between the pumping chamber 19 and port 29 to open to allow fluid to flow from the pumping chamber 19 to the cell containment chamber 7 via the port 29. When the pump 5 is released, negative pressure in the system simultaneously opens the valve or umbrella valve at the bottom portion of the pumping chamber 19 and closes the valve between the pumping chamber 19 and cell containment chamber 7.

In this embodiment, at rest, the interstitial fluid accumulation chamber 3 fills with accumulated fluid and fluid flows from the interstitial fluid accumulation chamber 3 to the pumping chamber 19. In addition, the cell containment chamber 7 is partially filled with nutrient fluid and Islet cells and insulin continues to flow out of the cell containment chamber 7 via a selective filter.

Figure 5:
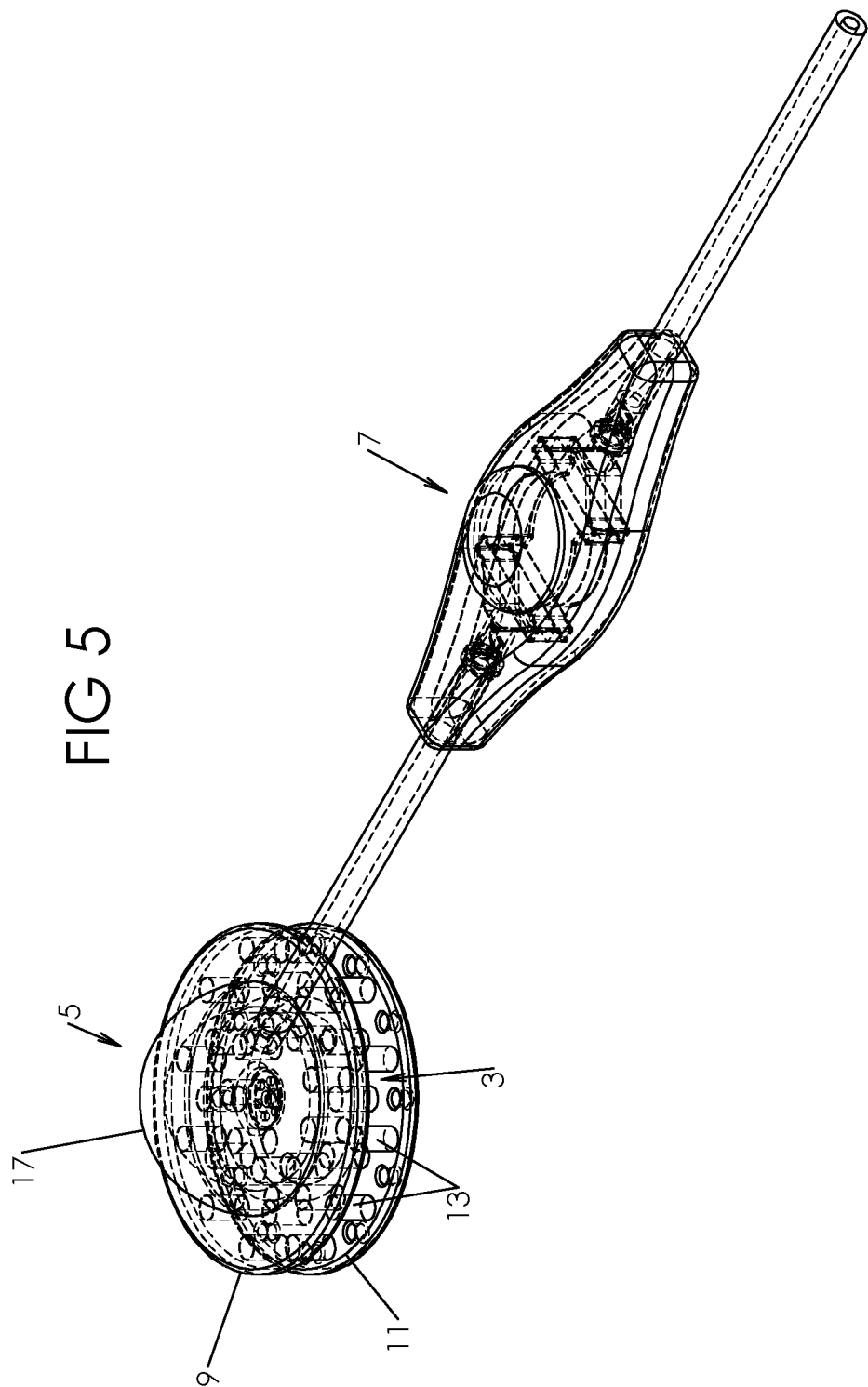
FIG. 5 is an isometric view of an embodiment of the present invention.
Figure 6:
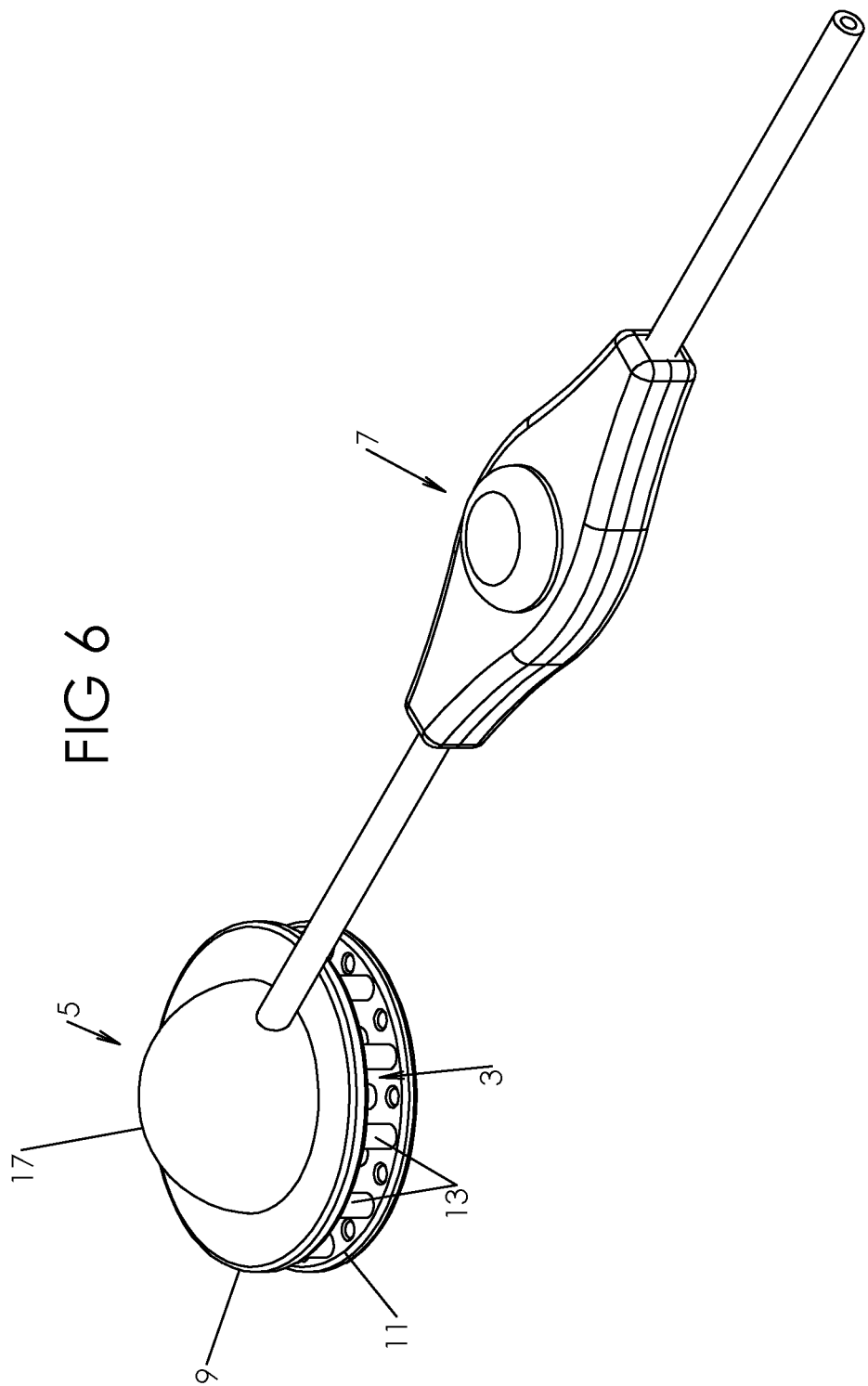
FIG. 6 is an isometric view of an embodiment of the present invention.

In the embodiment illustrated in FIGS. 5 and 6, the cell containment chamber 7 may not be in the same housing as the pump 5 and accumulation chamber 3. In such embodiment, when the system is at rest, the accumulation chamber 3 fills with nutrient rich interstitial fluid; the pump chamber 19 slowly fills with interstitial fluid as pressure in the accumulation chamber 3 increases. The cell chamber 7 is filled with used nutrient fluid. As the pump dome 17 is depressed, pressure forces open the valve between the pump 5 and accumulation chamber 3 to allow interstitial fluid to flow through to the cell containment chamber 7. New interstitial fluid flows into and fills the cell containment chamber 7 and old interstitial fluid and insulin flows out of the cell containment chamber 7 via the outlet catheter. When the pump 5 is released, negative pressure of the pump 5 release simultaneously opens valve to pump chamber 19 to refill with interstitial fluid and closes valve to the cell containment chamber 7 and insulin flow out of the cell containment chamber 7 ceases.

As illustrated in FIGS. 7, 8, 9, and 10, in another embodiment of the present invention, the interstitial fluid accumulation chamber 3 may be in an area detached from the pumping mechanism 5 and the isolation chamber 7, but connected to the pumping mechanism 5 through connection lines 33 or conduits for the fluid to be pumped through. In this embodiment the device can be two or three separate components as may be the case for the application. As such, the pumping mechanism 5 may be located in an area convenient for the patient's use while the accumulation chamber 3 and the isolation chamber 7 may be located in more suitable locations such as an area that is protected and where abundant interstitial fluid may accumulate.

Figure 7:
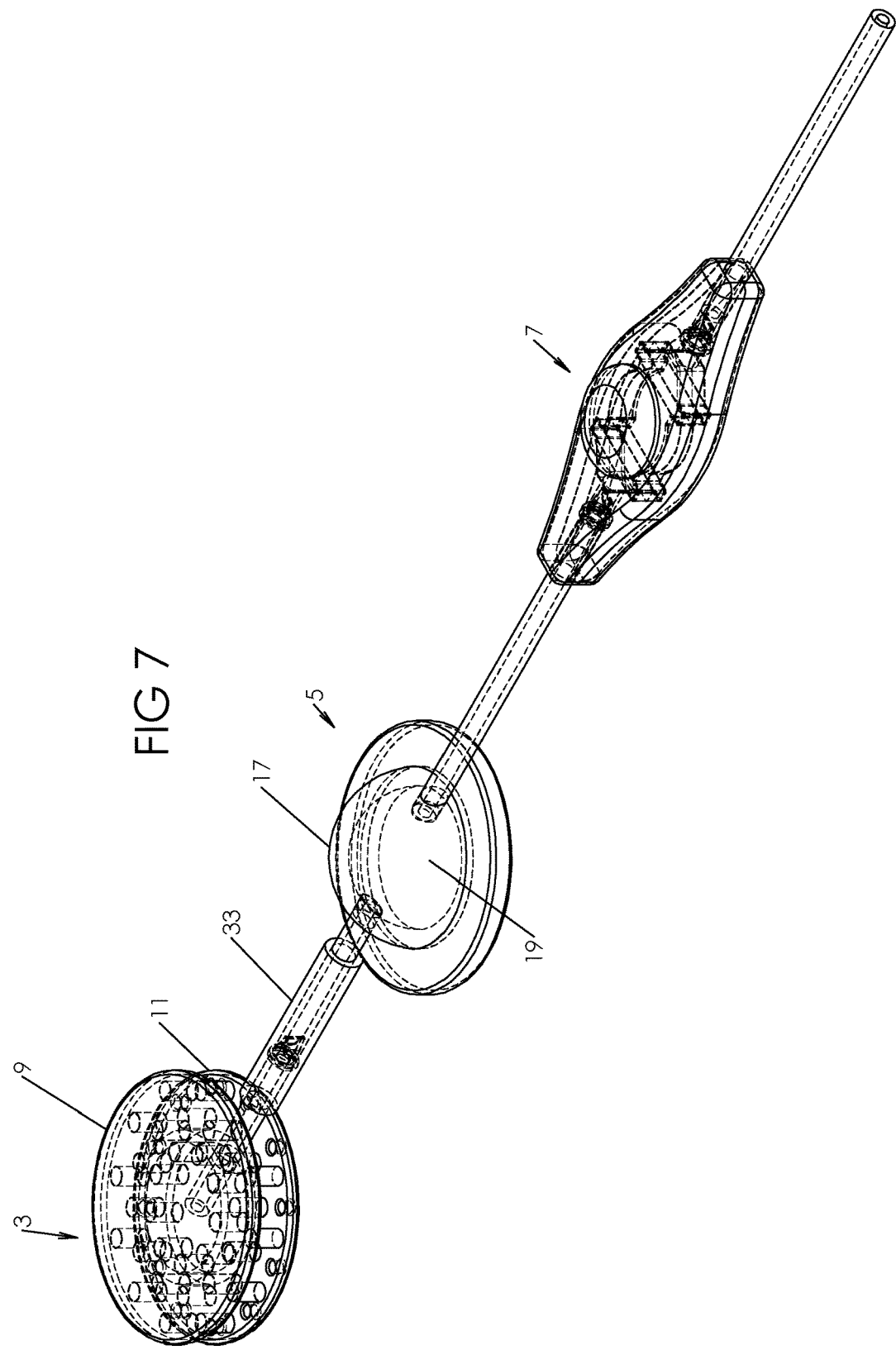
FIG. 7 is an isometric view of an embodiment of the present invention.
Figure 8:
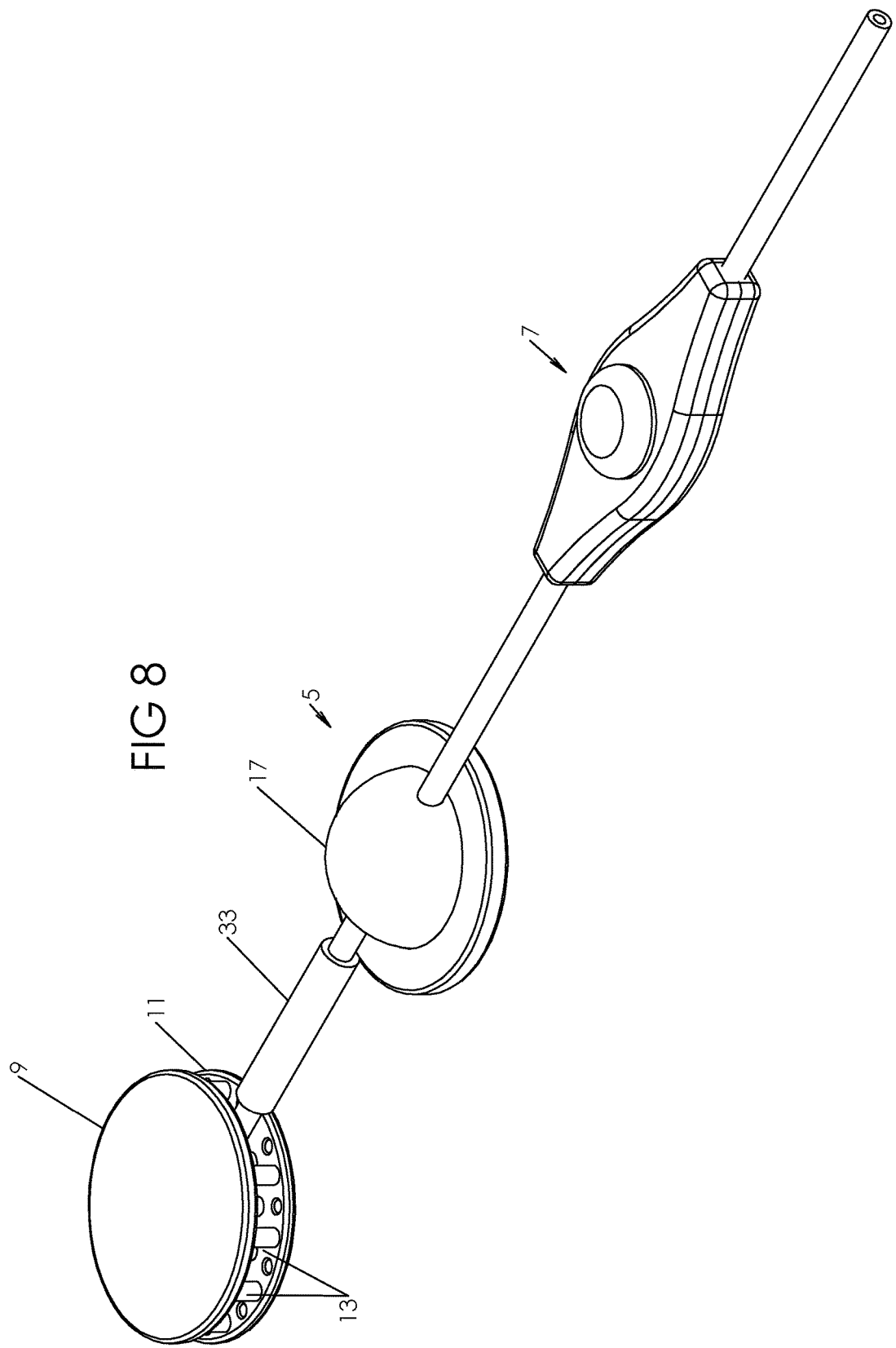
FIG. 8 is an isometric view of an embodiment of the present invention.

In the embodiment illustrated in FIGS. 7 and 8, the components of the present invention are placed in a linear fashion wherein the accumulation chamber/area 3 is at one end and the cell containment chamber 7 is at the opposite end. In this embodiment, when the system is at rest, the accumulation chamber 3 fills with nutrient rich interstitial fluid; the pump chamber 19 slowly fills with interstitial fluid as pressure in the accumulation chamber 3 increases. The cell chamber 7 is filled with used nutrient fluid. As the pump dome 17 is depressed, pressure forces open the valve between the pump 5 and cell chamber 7 while closing valve between pump 5 and accumulation chamber to allow interstitial fluid to evacuate to cell chamber 7.

New interstitial fluid flows into and fills the cell containment chamber 7 and old interstitial fluid and insulin flows out of the cell containment chamber 7. When the pump 5 is released, negative pressure of the pump 5 release simultaneously opens valve to pump chamber 19 to refill with interstitial fluid and closes valve to the cell containment chamber 7 and insulin flow out of the cell containment chamber 7 ceases.

Figure 9:
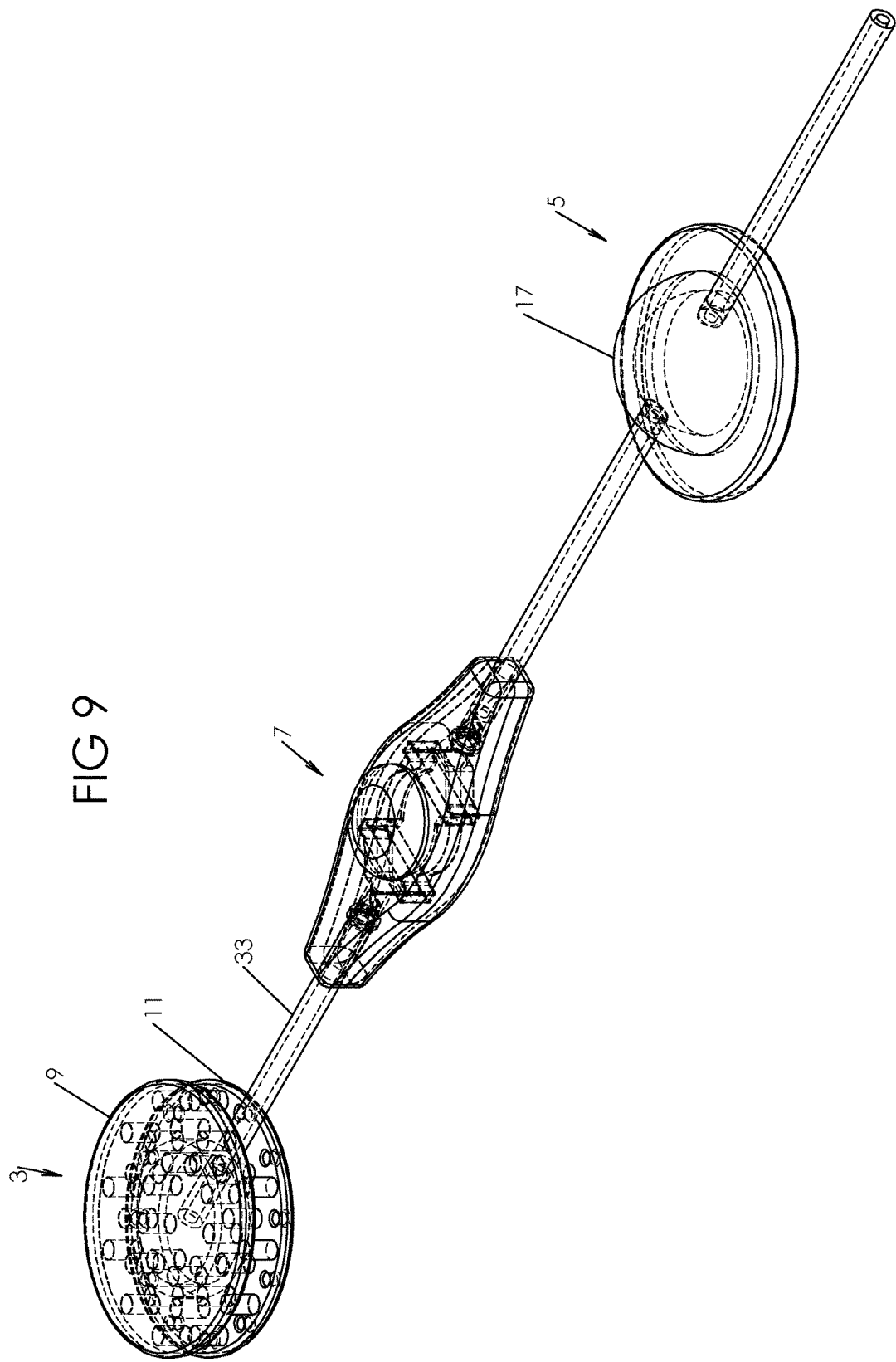
FIG. 9 is an isometric view of an embodiment of the present invention.
Figure 10:
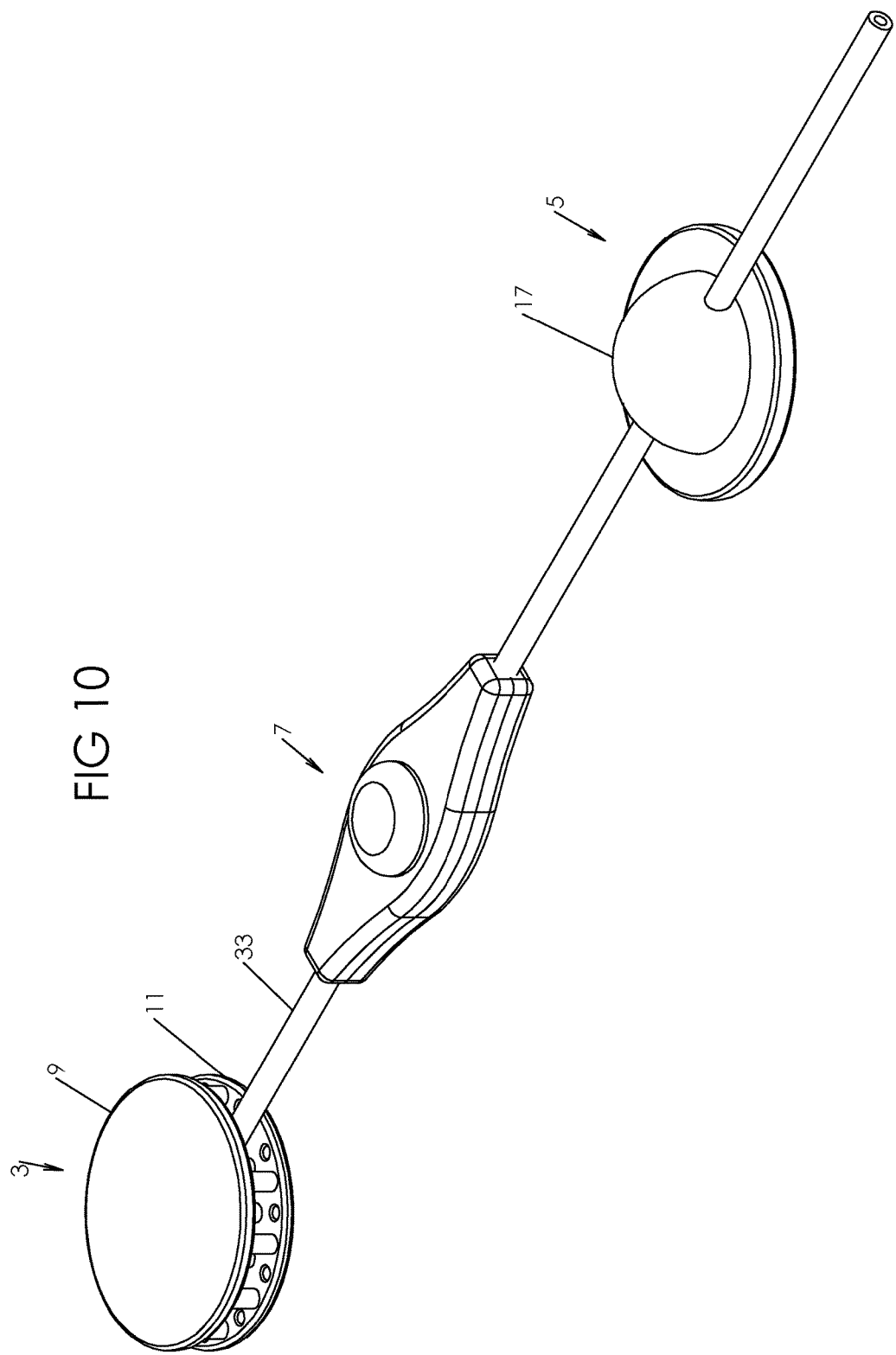
FIG. 10 is an isometric view of an embodiment of the present invention.

In the embodiment illustrated in FIGS. 9 and 10, the components of the present invention are placed in a linear fashion wherein the accumulation chamber/area 3 is at one end and the pump 5 is at the opposite end. In this embodiment, when the system is at rest, the accumulation chamber 3 fills with nutrient rich interstitial fluid; the cell chamber 7 slowly fills with interstitial fluid as pressure in the accumulation chamber 3 increases. The pump 5 is filled with used nutrient fluid. As the pump dome 17 is depressed, pressure forces used nutrient fluid and insulin in pump 5 to evacuate into the body. When the pump 5 is released, negative pressure of the pump 5 release simultaneously opens all valves allowing interstitial fluid from accumulation chamber 3 to flow into cell containment chamber 7 and interstitial fluid and insulin from cell containment chamber to flow into the pump 5.

In one embodiment, an outlet catheter 31 or tube leads out of the cell containment/isolation chamber 7 to be able to allow a user to have insulin delivered to any desired location in the body. The design of the present invention is innovative in that allows insulin produced by the cells in the cell containment chamber 7 to be delivered to a remote site if that is deemed the best therapeutic approach. Delivery of the insulin could be to the peritoneal cavity or the portal vein through the use of a special silicone catheter placed at the outlet side of the cell containment chamber is possible in this embodiment.

Another innovative aspect of the present invention is the use of a "port" 29 connected to the cell containment chamber 7 such that the transplanted cells can be delivered after the device has been allowed to stabilize within the host's body. With this port 29 or access point, the quality of the cells and the fluid within the chamber 7 can be monitored easily. It also allows researchers or physicians to monitor, adjust, remove, and/or reintroduce the cells or to simply add drugs to further enhance or adjust the health of the cells contained in the isolation chamber 7.

Figure 11:
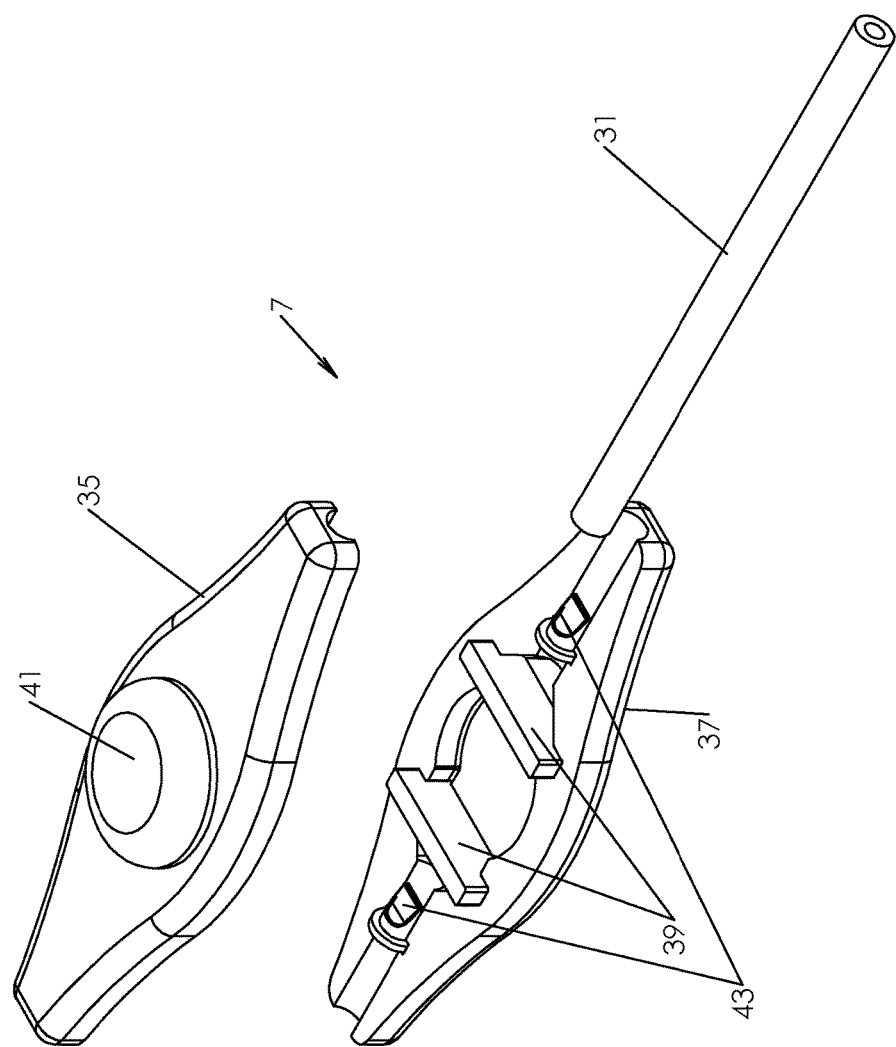
FIG. 11 is an isometric view of an embodiment of the present invention.
Figure 12:
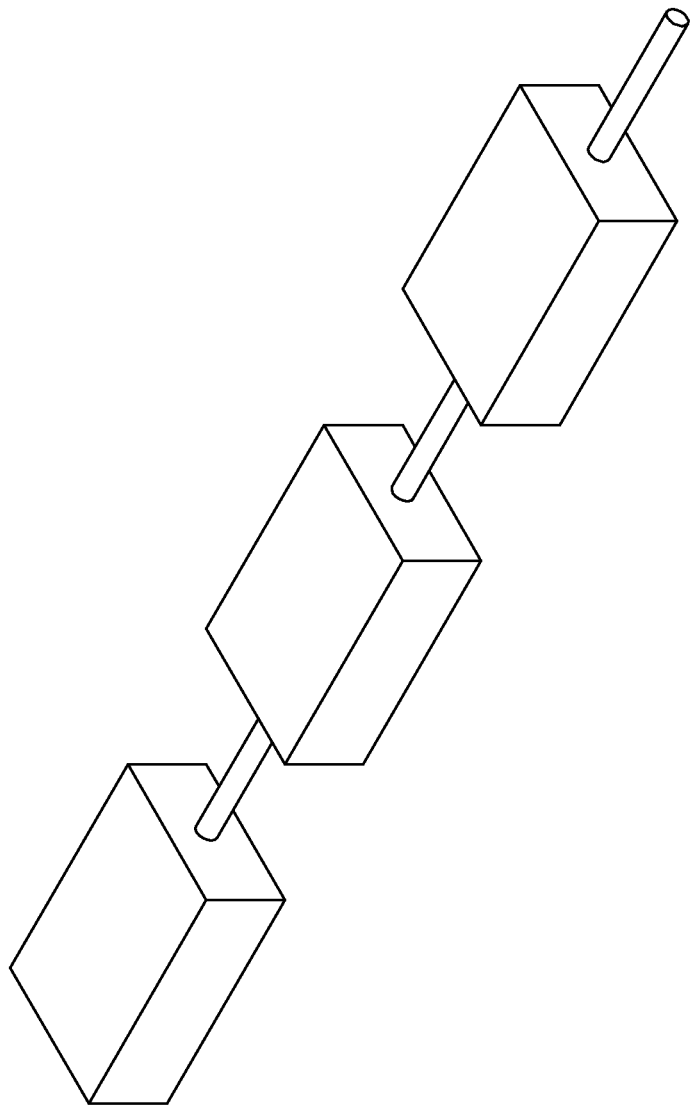
FIG. 12 is a schematic view of the present invention.

In one embodiment of the invention as illustrated in FIG. 11, the cell containment chamber 7 may have a top body 35, a bottom body 37 and an outlet catheter 31. The top body 35 has a septum 41 which serves as an access point through which the quality of the cells and the fluid within the chamber 7 can be monitored easily. The bottom body 37 has two selective filters 39 and two check valves 43, one at the entrance of the chamber 7 and one at the exit of the chamber 7.

Figure 13:
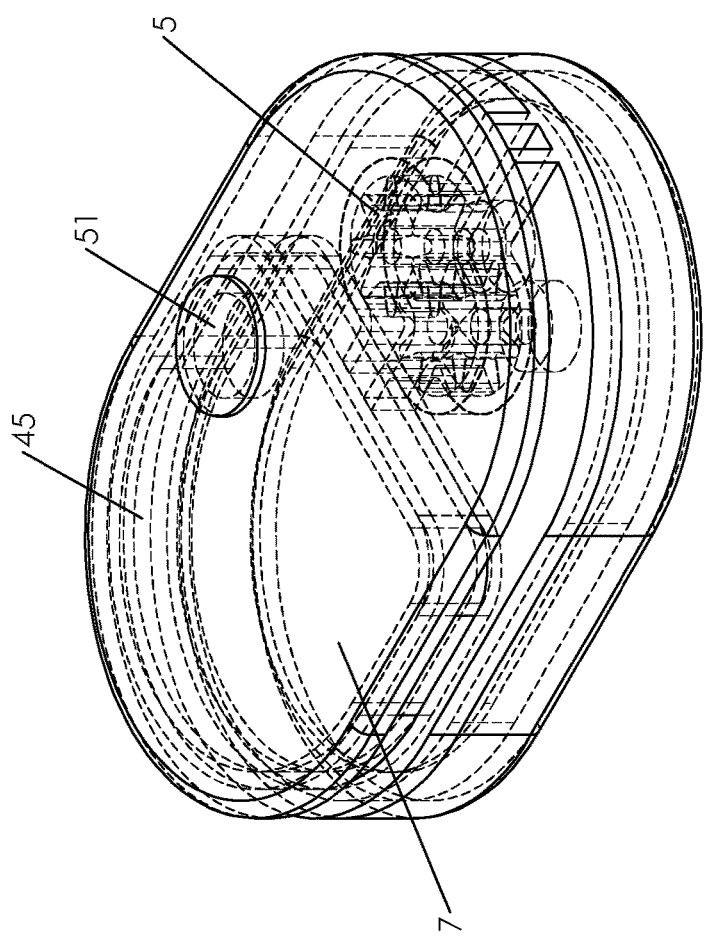
FIG. 13 is an isometric view of an embodiment of the present invention.
Figure 14:
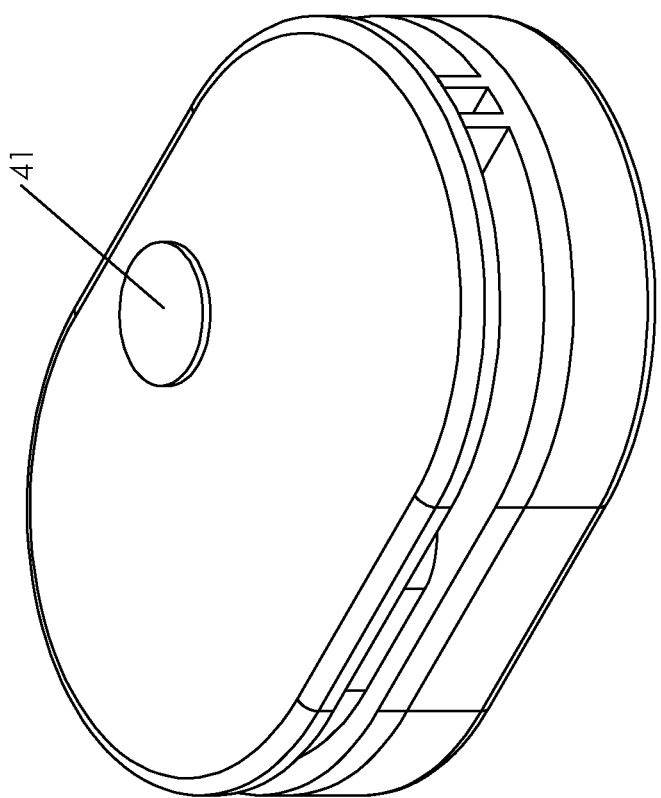
FIG. 14 is an isometric view of an embodiment of the present invention.

In a preferred embodiment as illustrated in FIGS. 13, 14 and 15, the accumulation chamber 3 and cell containment chamber/isolation chamber 7 occupy the same portion/area of the device. A selective filter 45 surrounds the entire cell containment chamber/isolation chamber 7. A pump 5 moves interstitial fluid out of the cell containment chamber/isolation chamber 7 to the body at a rate sufficient to supply the patient's body with insulin. The selective filter 45 is open to the patient's body which allows interstitial fluid to accumulate in the cell containment chamber/isolation chamber 7. As illustrated in FIGS. 13, 14, 15, the pump 5 may be a set of gears. The pump may be any conventional pumping means. In one embodiment, a circuit board 49 may house the electrical components necessary to control the rate of flow, provide power to the motors and/or recharge a power source. The present embodiment provides a septum 41 which serves as an access point through which the quality of the cells and the interstitial fluid within the cell containment chamber/isolation chamber 7 can be monitored easily.

Although only human applications have been discussed, it should be clear that the present invention may be easily used in veterinary applications or animal research and can be applied to both therapeutic use and research applications in any living body, human and animal.

What is claimed is:

1. An implantable apparatus configured to be implanted in any location inside of a human body for use as a protective environment for transplanted cells in a host body comprising of:
   a. an interstitial fluid accumulation chamber configured to allow interstitial fluid of the host body to flow continuously into the interstitial fluid accumulation chamber, the interstitial fluid accumulation chamber comprising: (1) spaced-apart plates; and/or (2) a plurality of posts forming a tortuous path for tissue to grow into while preventing the tissue from blocking an inlet or outlet of the interstitial fluid accumulation chamber;
   b. an isolation chamber for the transplanted cells; and
   c. at least one pumping mechanism having a dome shape pump configured to transfer the interstitial fluid from the interstitial fluid accumulation chamber to the isolation chamber and to transfer fluid produced by the isolation chamber to a desired location of the human body, wherein said at least one pumping mechanism is connected to the interstitial fluid accumulation chamber via a conduit, the at least one pumping mechanism comprising a pumping chamber having an inlet and an outlet; and
   d. a first valve disposed at the inlet of the pumping chamber between the interstitial fluid accumulation chamber and the pumping chamber and a a second valve disposed at the outlet of the pumping chamber between the pumping chamber and the isolation chamber, wherein when the dome shape pump is depressed, pressure forces open the first valve to allow the interstitial fluid to flow from the interstitial fluid accumulation chamber into the at least one pumping mechanism into the isolation chamber causing the fluid produced by the isolation chamber to flow out of the isolation chamber, and when the dome shape pump is released, negative pressure keeps the first valve open and closes the second valve so that the interstitial fluid fills the at least one pumping mechanism and the flow of the fluid, produced by the isolation chamber, out of the isolation chamber ceases.

2. The apparatus according to claim 1 wherein the interstitial fluid accumulation chamber and the isolation chamber occupy a same portion within the apparatus.

3. The apparatus according to claim 2 wherein the interstitial fluid accumulation chamber and the isolation chamber are partially enclosed by a filter.

4. The apparatus according to claim 3 wherein the entire filter is exposed to the host body.

5. The apparatus according to claim 3 wherein a portion of the filter is exposed to the host body.

6. The apparatus according to claim 2 wherein the interstitial fluid accumulation chamber and the isolation chamber are completely enclosed by a filter.

7. The apparatus according to claim 1 wherein the apparatus has a septum to access the isolation chamber.

8. The apparatus according to claim 7 wherein the septum is incorporated into the isolation chamber to access the isolation chamber.

9. The apparatus according to claim 1 wherein the at least one pumping mechanism is an electromechanical pump configured to draw the interstitial fluid from the interstitial fluid accumulation chamber to the isolation chamber.

10. The apparatus according to claim 1 wherein the at least one pumping mechanism is an electromechanical pump configured to draw the fluid produced by the isolation chamber from the isolation chamber to the host body.

11. The apparatus according to claim 10 wherein the electromechanical pump is controlled by a controller configured to control the volume and timing of the fluid, produced by the isolation chamber, being drawn from the isolation chamber.

12. The apparatus according to claim 11 wherein the apparatus is connected to a biofeedback system configured to control the volume and timing of the fluid, produced by the isolation chamber, being drawn from the isolation chamber.

13. The apparatus according to claim 1 wherein the at least one pumping mechanism is an electromechanical pump configured to draw the interstitial fluid from the interstitial fluid accumulation chamber to the isolation chamber, and to draw the fluid produced by the isolation chamber to the host body.

14. The apparatus according to claim 1 wherein the apparatus is constructed from a medical grade silicone.

15. The apparatus according to claim 1 wherein the apparatus is constructed from a biocompatible metallic material.

16. The apparatus according to claim 1 wherein the apparatus has outlet tubing configured to deliver the fluid, produced by the isolation chamber, to the desired location.

17. The apparatus according to claim 1 comprising (1) the spaced-apart plates.

18. The apparatus according to claim 1 comprising (2) the plurality of posts forming the tortuous path for the tissue to grow into while preventing the tissue from blocking the inlet or the outlet of the interstitial fluid accumulation chamber.

19. The apparatus according to claim 18 wherein the plurality of posts are cylindrical.

20. The apparatus according to claim 18 wherein the plurality of posts are disposed at different distances away from a center of the interstitial fluid accumulation chamber.

21. The apparatus according to claim 20 comprising a first plurality of posts disposed at a first distance away and around from the center of the interstitial fluid accumulation chamber, and a second plurality of posts disposed at a second distance away and around from the center of the interstitial fluid accumulation chamber, wherein the first and second distances are different.

22. The apparatus according to claim 21 wherein between each two of the second plurality of posts is disposed one of the first plurality of posts.

23. The apparatus according to claim 1 comprising (1) the spaced-apart plates; and (2) the plurality of posts forming the tortuous path for the tissue to grow into while preventing the tissue from blocking the inlet or the outlet of the interstitial fluid accumulation chamber.

24. The apparatus according to claim 23 wherein the plurality of posts extend from and between the spaced-apart plates.

25. The apparatus according to claim 24 wherein the plurality of posts are disposed around a periphery of the interstitial fluid accumulation chamber.

26. The apparatus according to claim 23 wherein the plurality of posts are cylindrical.

27. The apparatus according to claim 23 wherein the plurality of posts are disposed at different distances away from a center of the interstitial fluid accumulation chamber.

28. The apparatus according to claim 27 comprising a first plurality of posts disposed at a first distance away and around from the center of the interstitial fluid accumulation chamber, and a second plurality of posts disposed at a second distance away and around from the center of the interstitial fluid accumulation chamber, wherein the first and second distances are different.

29. The apparatus according to claim 28 wherein between each two of the second plurality of posts is disposed one of the first plurality of posts.

30. The apparatus according to claim 1 wherein the at least one pumping mechanism is configured to be operated manually by manually pressing the dome shape pump.

31. The apparatus according to claim 1 wherein the first and the second valves comprise one-way check valves.

32. The apparatus according to claim 1 wherein the isolation chamber comprises a filter which is porous to the fluid produced by the isolation chamber but which acts as a barrier to an immune system of the host body.

33. The apparatus according to claim 1 wherein the isolation chamber comprises a flexible, expandable elastomeric material.

34. A system for providing nutrients, nourishment and oxygen to transplanted cells using a human body's own interstitial fluid to provide such nourishment, oxygen and fluid maintenance for the transplanted cells comprised of:
  a. a first component to collect the interstitial fluid surrounding the system, the first component comprising: (1) spaced-apart plates; and/or (2) a plurality of posts forming a tortuous path for tissue to prow into while preventing the tissue from blocking an inlet or outlet of the first component;
  b. a second component to isolate transplanted cells;
  c. a pumping mechanism configured to transfer the interstitial fluid collected by the first component to the second component, wherein the second component and the pumping mechanism are connected via a conduit, the pumping mechanism comprising a pumping chamber having an inlet and an outlet; and
  d. a first valve disposed at the inlet of the pumping chamber between the first component and the pumping chamber and a second valve disposed at the outlet of the pumping chamber between the pumping chamber and the second component, wherein when the pumping mechanism is in one state, the first valve is open allowing the interstitial fluid to flow from the first component into the pumping mechanism into the second component causing a fluid produced by the second component to flow out of the second component, and when the pumping mechanism is in a second state, the first valve is open and the second valve is closed so that the interstitial fluid fills the pumping mechanism and the flow of the fluid produced by the second component out of the second component ceases.

35. The system according to claim 34 comprising (1) the spaced-apart plates.

36. The system according to claim 34 comprising (2) the plurality of posts forming the tortuous path for the tissue to grow into while preventing the tissue from blocking the inlet or the outlet of the first component.

37. The system according to claim 34 comprising (1) the spaced-apart plates; and (2) the plurality of posts forming the tortuous path for the tissue to grow into while preventing the tissue from blocking the inlet or the outlet of the first component.

38. An implantable apparatus to be implanted in any location inside of a human body for use as a protective environment for transplanted cells in a host body comprising of:
   a. an interstitial fluid accumulation chamber configured to allow interstitial fluid of the host body to flow continuously into the interstitial fluid accumulation chamber, the interstitial fluid accumulation chamber comprising: (1) spaced-apart plates; and/or (2) a plurality of posts forming a tortuous path for tissue to grow into while preventing the tissue from blocking an inlet or outlet of the interstitial fluid accumulation chamber;
   b. an isolation chamber for the transplanted cells having a single cavity which is connected to a pumping mechanism via a conduit; and
   c. the pumping mechanism configured to transfer the interstitial fluid from the interstitial fluid accumulation chamber to the isolation chamber, and to transfer fluid, produced by the isolation chamber, from the isolation chamber to a desired location of the human body, the pumping mechanism comprising a pumping chamber having an inlet and an outlet; and
   d. a first valve disposed at the inlet of the pumping chamber between the interstitial fluid accumulation chamber and the pumping chamber and a second valve disposed at the outlet of the pumping chamber between the pumping chamber and the isolation chamber, wherein when the pumping mechanism is in one state, the first valve is open allowing the interstitial fluid to flow from the interstitial fluid accumulation chamber into the pumping mechanism into the isolation chamber causing the fluid produced by the isolation chamber to flow out of the isolation chamber, and when the pumping mechanism is in a second state, the first valve is open and the second valve is closed so that the interstitial fluid fills the pumping mechanism and the flow of the fluid produced by the isolation chamber out of the isolation chamber ceases.

39. The apparatus according to claim 38 comprising (1) the spaced-apart plates.

40. The apparatus according to claim 38 comprising (2) the plurality of posts forming the tortuous path for the tissue to grow into while preventing the tissue from blocking the inlet or the outlet of the interstitial fluid accumulation chamber.

41. The apparatus according to claim 38 comprising (1) the spaced-apart plates; and (2) the plurality of posts forming the tortuous path for the tissue to grow into while preventing the tissue from blocking the inlet or the outlet of the interstitial fluid accumulation chamber.

42. An implantable apparatus to be implanted in any portion of a human body for use as a protective environment for transplanted cells in a host body comprising of:
   a. an interstitial fluid accumulation chamber configured to allow interstitial fluid of the host body to flow continuously into the interstitial fluid accumulation chamber, the interstitial fluid accumulation chamber comprising: (1) spaced-apart plates; and/or (2) a plurality of posts forming a tortuous path for tissue to grow into while preventing the tissue from blocking an inlet or outlet of the interstitial fluid accumulation chamber; and
   b. an isolation chamber for the transplanted cells having a single cavity wherein the interstitial fluid from the interstitial fluid accumulation chamber flows to the isolation chamber; and
   c. first and second valves disposed between the interstitial fluid accumulation chamber and the isolation chamber, wherein in one state, the first valve is open allowing the interstitial fluid to flow from the interstitial fluid accumulation chamber into the isolation chamber causing a fluid produced by the isolation chamber to flow out of the isolation chamber, and in a second state, the first valve is open and the second valve is closed so that the flow of the fluid produced by the isolation chamber out of the isolation chamber ceases.

43. The apparatus according to claim 42 comprising (1) the spaced-apart plates.

44. The apparatus according to claim 42 comprising (2) the plurality of posts forming the tortuous path for the tissue to grow into while preventing the tissue from blocking the inlet or the outlet of the interstitial fluid accumulation chamber.

45. The apparatus according to claim 42 comprising (1) the spaced-apart plates; and (2) the plurality of posts forming the tortuous path for the tissue to grow into while preventing the tissue from blocking the inlet or the outlet of the interstitial fluid accumulation chamber.

\* \* \* \* \*